United States Patent
Ptchelintsev

(10) Patent No.: US 7,825,157 B2
(45) Date of Patent: Nov. 2, 2010

(54) METHODS FOR IMPROVING THE AESTHETIC APPEARANCE OF SKIN

(75) Inventor: Dmitri Ptchelintsev, Jersey City, NJ (US)

(73) Assignee: Avon Products, Inc., New York, NY (US)

( * ) Notice: Subject to any disclaimer, the term of this patent is extended or adjusted under 35 U.S.C. 154(b) by 1571 days.

(21) Appl. No.: 11/026,198

(22) Filed: Dec. 30, 2004

(65) Prior Publication Data

US 2005/0118219 A1    Jun. 2, 2005

Related U.S. Application Data

(63) Continuation of application No. 10/033,169, filed on Dec. 27, 2001, now abandoned.

(51) Int. Cl.
| | |
|---|---|
| *A01N 43/16* | (2006.01) |
| *A61K 31/35* | (2006.01) |
| *A61K 8/02* | (2006.01) |
| *A61K 8/00* | (2006.01) |
| *A61K 8/18* | (2006.01) |
| *A61Q 17/04* | (2006.01) |
| *A61Q 1/00* | (2006.01) |
| *A61Q 1/12* | (2006.01) |

(52) U.S. Cl. .................. 514/455; 424/401; 424/59; 424/69

(58) Field of Classification Search ............ 514/455; 424/401, 59, 69
See application file for complete search history.

(56) References Cited

U.S. PATENT DOCUMENTS

| | | | |
|---|---|---|---|
| 5,268,176 A | 12/1993 | Znaiden et al. | |
| 5,698,206 A | 12/1997 | Becker et al. | |
| 5,709,847 A * | 1/1998 | Bissett et al. | 424/59 |
| 2003/0092675 A1 | 5/2003 | Duggan et al. | 514/63 |

FOREIGN PATENT DOCUMENTS

| | | |
|---|---|---|
| EP | 1284134 | 2/2003 |
| EP | 1396255 | 3/2004 |
| FR | 2754447 | 4/1998 |
| FR | 2774905 | 8/1999 |
| JP | 04244004 | 9/1992 |
| JP | 10072357 | 3/1998 |
| JP | 2000229857 | 8/2000 |
| JP | 2001226249 | 8/2001 |

OTHER PUBLICATIONS

Supplementary European Search Report dated Apr. 6, 2006.
Sakai, et al., "The Structure of garcinone E," Chem. Pharm. Bull. (1993). (Abstract only).
Mahabusarakam et al., "Antimicrobial activities of chemical constituents from Garcinia mangostana Linn," J. Sci. Soc. Thailand (1996). (Abstract only).

* cited by examiner

*Primary Examiner*—Sreeni Padmanabhan
*Assistant Examiner*—Kara R McMillian
(74) *Attorney, Agent, or Firm*—Charles J. Zeller; Joan M. McGillycuddy; Anthony M. Santini

(57) ABSTRACT

There are provided methods and compositions for improving the aesthetic appearance of akin, treating rosacea and/or telangiectasia, and treating the signs of dermatological aging. The method is directed to topically applying to an affected area an effective amount of mangostin, an analog thereof, or a combination thereof.

13 Claims, No Drawings

METHODS FOR IMPROVING THE AESTHETIC APPEARANCE OF SKIN

CROSS-REFERENCE TO A RELATED APPLICATION

The present application is a continuation application of U.S. Ser. No. 10/033,169, filed Dec. 27, 2001 now abandoned, which is incorporated herein by reference in its entirety.

BACKGROUND OF THE INVENTION

1. Field of the Invention

The present invention relates to methods for improving the aesthetic appearance of skin. The present invention further relates to methods of treating sensitive skin, methods of treating rosacea and/or telangiectasia, and methods of treating dermatological signs of aging. The present invention further relates the topical application of an effective amount of mangostin or an analog thereof.

2. Description of the Prior Art

Cosmetic products, which enhance the appearance of skin, are increasingly in demand. Consumers are interested in mitigating or delaying the signs of chronologically or hormonally aged or photo-aged skin, such as fine lines, wrinkles, drying, and sagging skin. During the aging process, the complexion of the skin, i.e., the color and appearance of the skin, deteriorates slowly from aging and/or exposure to sunlight.

Numerous cosmetic and medical treatments have been developed in an attempt to treat aged skin, as well as sensitive skin, rosacea, telangiectasia and related conditions. Rosacea and its clinical manifestations are known by those in the art. A description of rosacea and related literature is set forth in U.S. Pat. No. 5,972,993 at col. 1, line 15 through col. 2, line 55, which is incorporated herein by reference.

Telangiectasia typically presents as superficial cutaneous capillaries near the surface of the skin having a bright red center portion and branching radiations. Such a skin condition is often called "spider veins." When telangiectasia includes capillaries that are burst, leak blood or other fluids and/or become highly branched, the skin condition is commonly referred to as "broken capillaries." Telangiectasia may be spurred by UV exposure, stress, environmental conditions, injury and/or general skin aging.

The prior art discloses treatments for telangiectasia. U.S. Pat. No. 5,268,176 provides for treatment via repeated applications of a composition having inositol phosphoric acid or derivatives thereof. U.S. Pat. No. 5,698,206 provides for treatment via topical application of natural herbs in a carrier oil and concurrent ingestion of vitamin C.

Persons having rosacea and/or telangiectasia frequently address the skin irregularities brought on by those conditions by the application of cosmetics to mask the appearance of the skin. While the use of cosmetics is not deleterious to the health of the person, they do not mitigate or ameliorate the underlying conditions.

Mangostin has been employed in the prior art for a variety of purposes, but heretofore has not been employed to treat rosacea, telangiectasia, or aging skin. French Patent No. 2,754,447 relates to sunscreen compositions having mangostin. Japanese Patent Publication No. 10072357 relates to anti-allergenic agents and foods having mangostin. The publication, *Antimicrobial Activities of Chemical Constituents from Garcinia mangostana*, J. Sci. Soc. Thailand (1986), 12(4), pages 239-43, relates to the use of mangostin and mangostin derivatives as antimicrobials. The publication, *The Structure of Garcinone E*, Chem. Pharm. Bull. (1993), 41(5), pages 958-60, relates to the use of mangostin analogs as anti-tumor agents.

It would be desirable to have a topical composition to improve the aesthetic appearance of the skin. It would also be desirable to have an effective treatment for sensitive skin. It would also be desirable to have an effective treatment for rosacea and/or telangiectasia. It would also be desirable to have an effective treatment for the dermatological signs of aging.

SUMMARY OF THE INVENTION

It is an object of the present invention to provide a method for improving the aesthetic appearance of skin.

It is another object of the present invention to provide a method for treating sensitive skin.

It is also an object of the present invention to provide a method for treating rosacea.

It is also an object of the present invention to provide a method for treating telangiectasia.

It is still another object of the present invention to provide a method for treating the signs of dermatological aging.

These and other objects and advantages of the present invention are achieved by a method of topically applying to an affected area an effective amount of mangostin and/or an analog thereof.

These and other objects of the invention are also achieved by a method of topically applying to an affected area an effective amount of a natural extract of mangostin and/or an analog thereof.

DETAILED DESCRIPTION OF THE INVENTION

It was found surprising that there are methods for improving the appearance of skin, treating sensitive skin, treating rosacea and/or telangiectasia, and treating the signs of dermatological aging, particularly with respect to the face, legs and/or torso. It was also surprisingly found that such methods are effected by topically applying to the affected area an effective amount of mangostin or an analog thereof.

The terms "treating" or "treat" as used in the present invention mean reduce, diminish, ameliorate, or prevent. To improve skin appearance means to partially or fully restore the normal appearance of the skin.

Mangostin and its analogs are compounds that can be derived from natural sources (e.g., *Garcinia mangostana L., Guttiferae* as described in Schmid, Ann. 93, 83 (1855)) and/or synthesized.

Mangostin and its analogs can be represented by the following general formula:

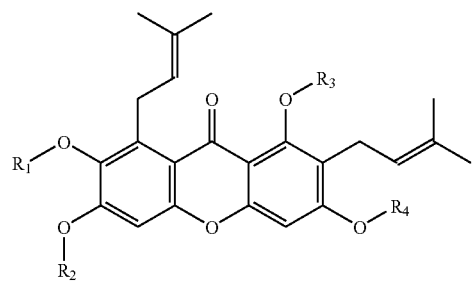

wherein $R_1$, $R_2$, $R_3$ and $R_4$ may, independently, be any of the following: a hydrogen atom; a carbohydrate; an acyl group, substituted or unsubstituted, straight-chain or branched, fully saturated or having one or more unsaturated bonds, that has from 1 to 22, preferably 1 to 18, and most preferably from 1 to 12, carbon atoms; an alkyl group, substituted or unsubstituted, straight-chain or branched, fully saturated or having one or more unsaturated bonds, that has from 1 to 22, preferably 1 to 18, and most preferably from 1 to 12, carbon atoms; an alkenyl group, substituted or unsubstituted, straight-chain or branched, fully saturated or having one or more unsaturated bonds, that has from 1 to 22, preferably from 1 to 18, and most preferably from 1 to 12 carbon atoms; an alkynyl group, substituted or unsubstituted, straight-chain or branched, fully saturated or having one or more unsaturated bonds, that has from 1 to 22, preferably 1 to 18, and most preferably from 1 to 12, carbon atoms; a phenyl group, substituted or unsubstituted; a benzyl group, substituted or unsubstituted; a cycloalkyl group, substituted or unsubstituted, that has from 3 to 8, preferably from 4 to 7, and most preferably from 5 to 6, carbon atoms; a cycloalkenyl group, substituted or unsubstituted, that has from 4 to 8, preferably from 4 to 7, and most preferably from 5 to 6, carbon atoms; and an oxaalkyl, oxaalkenyl, or oxaalkynyl group having at least one oxygen atom in its backbone structure, substituted or unsubstituted, and straight-chained or branched. Suitable carbohydrates include but are not limited to glucose, lactose, fructose, rhamnose, trehalose, or fucose. Glucose and fucose are preferred carbohydrates. Preferably, at least two of $R_1$, $R_2$, $R_3$ and $R_4$ are hydrogen atoms. Most preferably, $R_1$ is an alkyl group or acyl group having from 1 to 12 carbon atoms and $R_2$, $R_3$ and $R_4$ are each hydrogen atoms.

Mangostin has the chemical name of 1,3,6-trihydroxy-7-methoxy-2,8-di(3-methyl-2-butenyl)xanthone or, alternately, 1,3,6-trihydroxy-7-methoxy-2,9-bis(3-methyl-2-butenyl)-9H-xanthen-9-one. The physical properties of mangostin are set forth in The Merck Index, 10th Edition (1983), page 818, which is incorporated herein by reference.

Analogs of mangostin can be derived from plant or natural sources or be prepared via conventional organic synthesis procedures such catalytic esterification, ethoxylation, and etherification. Such analogs include the following: alpha mangostin, beta mangostin, bicyclomangostin, gamma mangostin, 3-O-methylmangostin, mangostin triacetate, and mangostin-3,6-di-O-glucoside.

In the present method, mangostin and/or its analogs can be topically applied without a vehicle, i.e. in an amount 100 percent by weight (wt %). More preferably, mangostin and/or its analogs are admixed with a vehicle suitable to form a composition for topical application. When compositions are employed, the composition preferably has about 0.0001 wt % to less than 100 wt %, more preferably about 0.0001 wt % to about 90 wt %, still more preferably about 0.01 wt % to about 50 wt %, and most preferably about 0.5 wt % to about 20 wt %, of mangostin and/or its analogs based on the total weight of the composition.

In the present invention, mangostin and/or its analogs can be used to improve the overall appearance of the skin and treat sensitive skin. Treatable skin conditions include itch, irritation, inflammation, loss of tone (e.g., sagging and/or uneven color), redness, allergic responses, combination (oil/dry/unbalanced) skin, blemishes, flushing and blushing.

Also in the present invention, mangostin and/or its analogs can be used to treat dermatological signs of aging due to, for example, chronological aging, hormonal aging and/or photoaging. Such signs of aging include, but are not limited to, skin fragility; loss of collagen and/or elastin; skin atrophy; appearance and/or depth of lines and/or wrinkles including fine lines; skin discoloration including dark eye circles; skin sagging; skin fatigue and/or stress, e.g., skin breakout due to environmental stress, such as pollution and/or temperature changes; loss of skin tone, clarity or luster; loss of skin firmness; poor skin texture; loss of skin elasticity and/or resiliency; and thin skin.

The compositions of the present invention can be effectively applied daily for about 1, 2 or 4 weeks, or more. Preferably, the compositions are applied daily for about 2 weeks.

Compositions useful in the present method can be formulated in any suitable product form. Such product forms include, but are not limited to, aerosol spray, cream, dispersion, foam, gel, lotion, mask, mousse, ointment, powder, patch, pomade, solution, pump spray, stick, tape and towelette.

Compositions useful in the present method can include a vehicle that is pharmaceutically or cosmetically acceptable. Such vehicles include, but are not limited to, one or more $C_{1-4}$ alcohols, fatty alcohols, fatty ethers, fatty esters, polyols, glycols, vegetable oils, mineral oils, liposomes, laminar lipid materials, silicone oils, water, or any combinations thereof.

Optionally, compositions useful in the present method can include one or more of the following additional ingredients: amino acids, anesthetics, anti-acne agents, anti-allergenics, antifungals, antimicrobials, anti-inflammatory agents, anti-irritants, antineoplastics, antioxidants, antiseptics, antivirals, chelating agents, colorants, depigmenting agents, emollients, emulsifiers, exfoliants such as oxa acids and alpha and beta hydroxy acids, film formers, fragrances, humectants, hypopigmenting agents, immune system boosting agents, immune system suppressing agents, insect repellents, lubricants, moisturizers, pharmaceutical agents, photostabilizing agents, preservatives, retinoids, skin protectants, skin penetration enhancers, staining agents, sunscreens, stabilizers, surfactants, thickeners, viscosity and/or rheology modifiers, vitamins, or any combinations thereof.

The following are examples of the present invention.

EXAMPLE 1

| Oil-in-Water Emulsion | wt % |
| --- | --- |
| Humectant (e.g. Glycols, Glycerols) | 0.5-15 |
| Thickeners (e.g. Gums, Starches, Polymers) | 0.1-4 |
| Chelants (e.g. Disodium EDTA, Tetrasodium EDTA) | 0.001-0.5 |
| Preservatives | 0.01-2 |
| Sunscreen (e.g. Parsol 1789 ™, ethylhexylmethoxycinnamate, benzophenone-3) | 0.1-50 |
| Silicone | 0.1-15 |
| Silica | 0.01-10 |
| Extracts (e.g., one or more of Pomegranate extract, Neem Seed Cell Broth, Grape Seed Extract, Salvia Miltiorrhiza Extract, Iris Florentina Root Extract, Carrot Extract, Cucumber Extract, White Birch (Betula Alba) Bark Extract, Rosemary Extract, Algae Extract, or any combination) | 0.0001-50 |
| Fatty alcohol/Emulsifers/Wax/Fatty acid (e.g. ceteth-20 phosphate/cetearyl alcohol/dicetyl phosphate, Tribehenin PEG-20 Ester, sodium Dihydroxyethyl phosphate, cetearyl glocoside, cocoglyceride) | 0.5-15 |
| Emulsion Stabilizers/Viscosity Modifiers (e.g. acrylates/$C_{10-30}$ alkyl acrylate crosspolymer, acrylate/aminoacrylates/$C_{10-30}$ alkyl PEG-20 itaconate, sodium acrylate/ | 0.1-20 |

-continued

| Oil-in-Water Emulsion | wt % |
|---|---|
| acryloyldimethyl taurate copolymer, acrylates/C$_{10-30}$ alkyl acrylate crosspolymer | |
| Film Formers (e.g. decene/butene copolymer, acrylates/octylacrylamide copolymer, adipic acid/diethylene glycol/glycerin crosspolymer) | 0.001-2 |
| Emollients | 0.1-20 |
| Mangostin | 0.5-20 |
| Demineralized Water | Q.S. |

EXAMPLE 2

| Water/Silicone Emulsion | wt % |
|---|---|
| Sodium PCA 50% | 0.1-4 |
| Sodium Lactate 60% | 0.01-10 |
| Sodium Chloride | 0.1-10 |
| Humectant(Glycerin, Glycols, Glycerols) | 0.5-10 |
| Ammonium Hydroxide | 0.01-10 |
| Cyclomethicone | 0.1-20 |
| Cyclomethicone/Dimethicone Copolyol | 0.1-20 |
| Emollients (E.G. Cetyl Octanoate) | 0.1-20 |
| Dimethicone Copolyol/Cyclopentasiloxane | 0.1-10 |
| Alpha mangostin | 0.01-50 |
| Demineralized Water | Q.S. |

EXAMPLE 3

| Gel | wt % |
|---|---|
| Carbopol ™ | 0.01-3 |
| Glycerin | 0.1-30 |
| Butylene Glycol | 0.1-30 |
| Disodium EDTA | 0.01-2 |
| Methylparaben | 0.01-2 |
| Hydroxyethyl Cellulose | 0.01-2 |
| Corn (Zea Mays) Starch | 0.01-10 |
| C.S. D&C Yellow No. 10 | 0.001-1 |
| C.S. FD&C Blue No. 1 | 0.001-1 |
| POE (20 M) Methyl Glucose Ether | 0.01-10 |
| Dimethyl Polysiloxane | 0.01-10 |
| Peg 50 Shea Butter | 0.01-10 |
| Sodium Hydroxide Solution | 0.01-5 |
| Benzyl Alcohol | 0.01-5 |
| Mangostin triacetate | 0.001-10 |
| Demineralized Water | Q.S. |

EXAMPLE 4

| Cleansing Foam | wt % |
|---|---|
| Humectant (Glycerin, Butylene Glycol) | 5-25 |
| Polyethylene Glycol | 0.1-20 |
| Bentonite | 0.1-20 |
| Stearic Acid | 0.1-30 |
| Myristic Acid | 0.1-20 |
| Cetearyl Alcohol/Ceteareth-20 | 1 |
| Potassium Hydroxide 45% | 0.1-20 |

-continued

| Cleansing Foam | wt % |
|---|---|
| Preservatives (E.G. Benzyl Alcohol, 2-Phenoxyethanol, Benzyl Alcohol) | 0.1-10 |
| Alpha mangostin | 0.15-20 |
| Demineralized Water | Q.S. |

| | wt % |
|---|---|
| Mixed tocopherols | 1 |
| Vitamin E succinate 1000 PEG | 0.5 |
| Gamma Oryzanol | 0.2 |
| Lipoic Acid | 0.1 |
| Hesperetin | 0.1 |
| Naringenin | 0.1 |
| Silybin (Silymarin) | 0.1 |
| Chlorogenic Acid | 0.01 |
| Mangostin | 0.001-20 |
| Vehicle | Q.S. |

EXAMPLE 6

| Moisturizing Cream | wt % |
|---|---|
| Propyl gallate | 1 |
| Rosmantic acid | 5 |
| N-actyl-cysteine | 3.5 |
| Beta-carotene | 0.001 |
| Licorice root extract | 0.01 |
| Naringenin | 2.7 |
| PPG Myristyl Ether Propionate | 6.5 |
| Oleyl alcohol | 3.5 |
| Stearic acid | 8.6 |
| Lanolin | 1 |
| Pomegranate Extract | 0.00-2 |
| Neem Seed Cell Broth | 0.01-10 |
| Grape Seed Extract | 0.01-2 |
| Salvia Miltiorrhiza Extract | 0.00-10 |
| Iris Florentina Root Extract | 0.00-20 |
| Carrot Extract | 0.00-2 |
| Cucumber Extract | 0.00-2 |
| White Birch (Betula Alba) Bark Extract | 0.00-2 |
| Rosemary Extract | 0.00-2 |
| Algae Extract | 0.00-2 |
| Glycerin | 2.5 |
| Triethanolamine | 0.5 |
| Germal | 0.1 |
| Methylparaben | 0.01 |
| Mangostin | 0.001-20 |
| Demineralized water | Q.S. |

EXAMPLE 7

| Moisturizing Cream | wt % |
|---|---|
| Tocopherol | 2 |
| Quercetin/Lycopene | 2.5 |
| Carbopol ™ | 0.3 |
| Triethanolamine | 0.5 |
| Mineral Oil | 1.5 |
| Safflower oil | 0.3 |
| Squalene | 1.7 |
| Dimethicone | 0.7 |

-continued

| Moisturizing Cream | wt % |
| --- | --- |
| Allantoin | 1 |
| Oleyl alcohol | 0.6 |
| Cholesterol | 4.5 |
| Lanolin oil | 0.6 |
| Mangostin | 0.001-20 |
| Vehicle | Q.S. |

It should be understood that the foregoing description is only illustrative of the present invention. Various alternatives and modifications can be devised by those skilled in the art without departing from the invention. Accordingly, the present invention is intended to embrace all such alternatives, modifications and variances which fall within the scope of the appended claims.

What is claimed is:

1. A method for reducing, diminishing, or ameliorating telangiectasia, comprising topically applying to an affected area of the skin an effective amount of a composition having a first ingredient represented by the following formula:

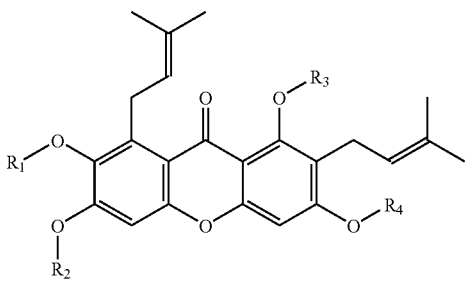

wherein $R_1$, $R_2$, $R_3$ and $R_4$ may, independently, be a hydrogen atom; a carbohydrate; an acyl group, substituted or unsubstituted, straight-chain or branched, fully saturated or having one or more unsaturated bonds, and have from 1 to 22 carbon atoms; an alkyl group, substituted or unsubstituted, straight-chain or branched, fully saturated or having one or more unsaturated bonds, and have from 1 to 22 carbon atoms; an alkenyl group, substituted or unsubstituted, straight-chain or branched, fully saturated or having one or more unsaturated bonds, and have from 1 to 22 carbon atoms; an alkynyl group, substituted or unsubstituted, straight-chain or branched, fully saturated or having one or more unsaturated bonds, and have from 1 to 22 carbon atoms; a phenyl group, substituted or unsubstituted; a benzyl group, substituted or unsubstituted; a cycloalkyl group, substituted or unsubstituted, and have from 3 to 8 carbon atoms; a cycloalkenyl group, substituted or unsubstituted, and have from 4 to 8 carbon atoms; and an oxaalkyl, oxaalkynyl, or oxaalkynyl group having at least one oxygen atom in its backbone structure, substituted or unsubstituted, and straight-chained or branched;

a second ingredient selected from the group consisting of at least one of an antioxidant, a depigmenting agent, an anti-inflammatory agent, a vitamin, and an anti-irritant; and a cosmetically acceptable vehicle.

2. The method of claim 1, wherein at least two of $R_1$, $R_2$, $R_3$ and $R_4$ are hydrogen atoms.

3. The method of claim 1, wherein $R_1$ is an alkyl group or an acyl group having from 1 to 12 carbon atoms, and wherein $R_3$ and $R_4$ are each hydrogen atoms.

4. The method of claim 1, wherein the composition is in a product form selected from the group consisting of aerosol spray, cream, dispersion, foam, gel, lotion, mask, mousse, ointment, powder, patch, pomade, solution, pump spray, stick, tape, and towelette.

5. The method of claim 1, wherein the first ingredient is present in an amount from about 0.0001 wt % to about less than 100 wt % based on the total weight of the composition.

6. The method of claim 1, wherein the first ingredient is present in an amount from about 0.0001 wt % to about 90 wt % based on the total weight of the composition.

7. The method of claim 1, wherein the first ingredient is present in an amount from about 0.01 wt to about 50 wt % based on the total weight of the composition.

8. The method of claim 1, wherein the first ingredient is present in an amount from about 0.5 wt % to about 20 wt % based on the total weight of the composition.

9. The method of claim 1, wherein the first ingredient is 1,3,6-trihydroxy-7-methoxy-2,8-di(3-methyl-2-butenyl) xanthone.

10. The method of claim 1, wherein the telangiectasia includes the appearance of spider veins, broken capillaries or both.

11. The method of claim 1, wherein the composition is applied for an effective period of time.

12. The method of claim 1, wherein the composition is applied daily for about 1 week.

13. The method of claim 1, wherein the composition is applied daily for about 2 weeks.

* * * * *